United States Patent
Burton et al.

(10) Patent No.: US 7,071,328 B2
(45) Date of Patent: Jul. 4, 2006

(54) METHOD FOR THE PREPARATION OF 21-HYDROXY-6,19-OXIDOPROGESTERONE (21 OH-6OP)

(75) Inventors: Gerardo Burton, Florida (AR); Carlos P. Lantos, Buenos Aires (AR); Adriana Silvia Veleiro, Martinez (AR)

(73) Assignee: Applied Research System ARS Holding N.V., Curacao (AR)

( * ) Notice: Subject to any disclaimer, the term of this patent is extended or adjusted under 35 U.S.C. 154(b) by 70 days.

(21) Appl. No.: 10/380,167

(22) PCT Filed: Sep. 17, 2001

(86) PCT No.: PCT/EP01/10734

§ 371 (c)(1),
(2), (4) Date: Jul. 18, 2003

(87) PCT Pub. No.: WO02/22646

PCT Pub. Date: Mar. 21, 2002

(65) Prior Publication Data
US 2004/0092733 A1 May 13, 2004

(30) Foreign Application Priority Data
Sep. 18, 2000 (EP) ............................................ 00119494

(51) Int. Cl.
*A61K 31/56* (2006.01)
*C07J 7/00* (2006.01)
*C07J 1/00* (2006.01)

(52) U.S. Cl. ........................... 540/5; 514/180; 514/181; 514/172; 514/179; 540/56

(58) Field of Classification Search ................. 514/179, 514/180, 181
See application file for complete search history.

(56) References Cited

U.S. PATENT DOCUMENTS

| 4,814,333 | A | * | 3/1989 | Ravaris | 514/254.07 |
| 6,150,349 | A | * | 11/2000 | Schatzberg et al. | 514/179 |
| 6,303,591 | B1 | * | 10/2001 | Burton et al. | 514/179 |
| 6,380,155 | B1 | * | 4/2002 | Al Barazanji | 514/2 |
| 2004/0029846 | A1 | * | 2/2004 | Burton et al. | 514/172 |
| 2004/0092733 | A1 | * | 5/2004 | Burton et al. | 540/5 |

FOREIGN PATENT DOCUMENTS

EP 0 903 146 3/1999

OTHER PUBLICATIONS

Adriana S. Veleiro et al.: "Synthesis of d21–hydroxy–11,19–oxidopregn–4–ene–3,20–dione and 21–hydroxy–6,19–oxidopregn–4–ene3,20dione" STEROIDS, vol. 60, No. 3, pp. 268–271, 1995.

S.C.P. Costa et al.: "Ultrasound assisted remote functionalization of non–activated carbon atoms: efficient in situ formation of tetrahydrofurans by sonolysis of bromohydrins with (diacetoxyiodo)benezen/I2" Tetrahedron Letters, vol. 40, No. 49, pp. 8711–8714, Dec. 3, 1999.

(Continued)

*Primary Examiner*—Sabiha N. Qazi
(74) *Attorney, Agent, or Firm*—Oblon, Spivak, McClelland, Maier & Neustadt, P.C.

(57) ABSTRACT

The present invention relates to a novel method for preparing 21-hydroxy-6,19-oxidopro-gesterone (21OH-6OP) and/or its 21-acetate, 21-propionate, 21-hemisuccinate, 21-phosphate, 21-oleate derivatives. 21OH-6OP and its ester derivatives are antiglucocorticoids for the treatment or prophyl axis of diseases associated to an excess of glucocorticoids, in particular for treating Cushing's syndrome, iatrogenic hypercortisolism or depression.

12 Claims, 1 Drawing Sheet

OTHER PUBLICATIONS

Figure 1:
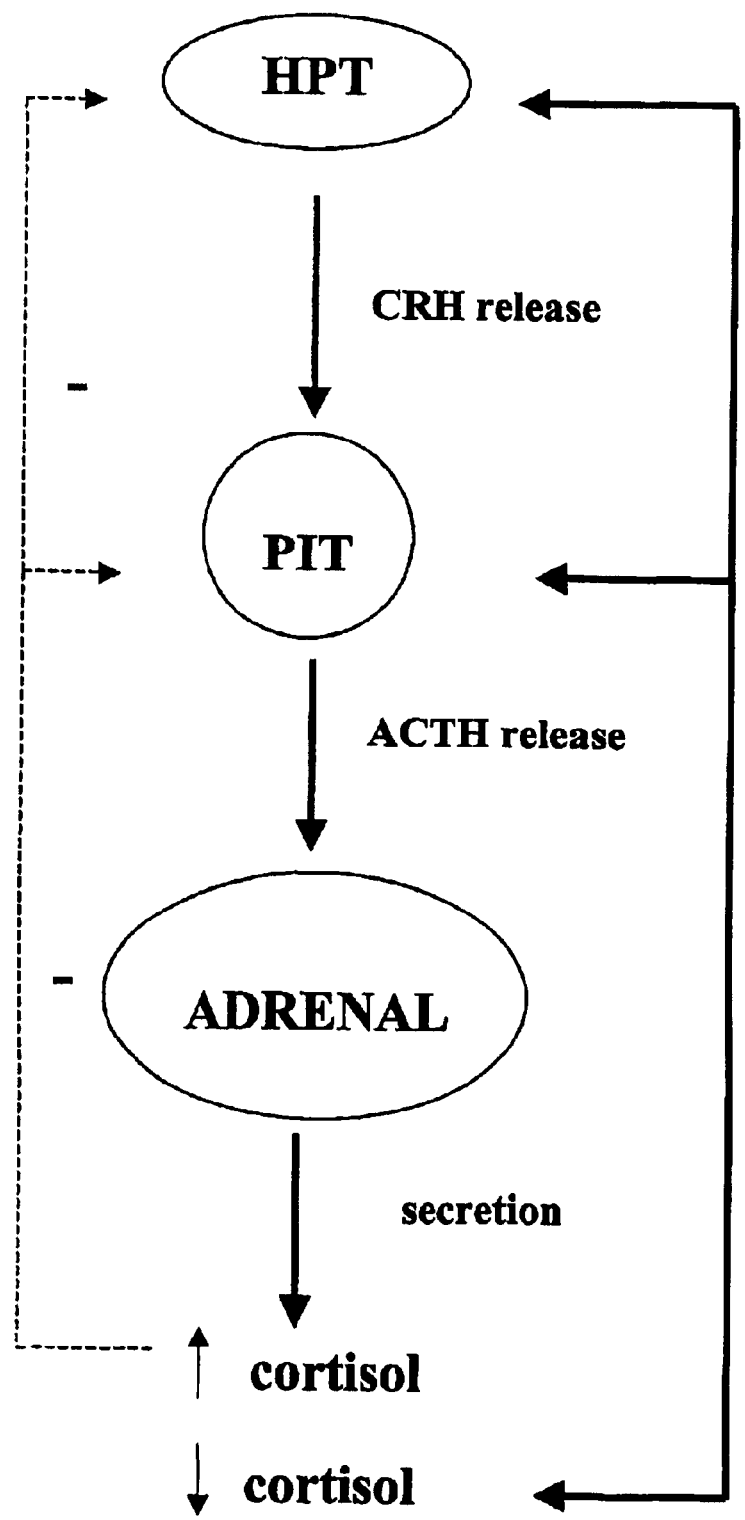

Pedro De Armas et al.: "Intramolecular hydrogen abstraction. Hypervalent organoiodine compounds, convenient reagents for alkoxyl radical generation" J. Chem. Soc., Perkin Trans. 1, vol. 3, pp. 405–411, 1989.

Jose I. Concepcion et al.: "Intramolecular hydrogen abstraction. Iodosobenzene diacetate, an efficient and convenient reagent for alkoxy radical generation" Tetrahedron Lett., vol. 25, No. 18, pp. 1953–1956, 1984.

D.B. Gower: "Modifiers of steroid–hormone metabolism: a review of their chemistry, biochemistry and clinical applications" J. Steroid Biochem., vol. 5, p. 501, 1974.

Barry M. Forman et al.: "Nuclear hormone receptor activate direct, inverted and everted repeats" Annals of New–York Academy of Science, vol. 761, pp. 29–37, 1995.

Jeffrey L. Arriza et al.: "Cloning of human mineralocorticoid receptor complementary DNA: structural and functional kinship with the glucocorticoid receptor" SCIENCE, vol. 237, pp. 268–275, 1987.

G. Teutsch, et al.: "General structure–activity correlations of antihormones" Annals of New–York Academy of Science, vol. 761, pp. 5–28, 1995.

VIII International Congress of Pharmacology, Tokyo, Japan Abstract, 1981.

Irvin M. Spitz et al.: "Mifepristone (RU 486)—A modulator of progestin and glucocorticoid action" N. Engl, J. Med., vol. 329, pp. 404–412, 1993.

Physiopathology of Endocrine Diseases and Mechanisms of Hormone Acton By Alan R. Liss, New York, pp. 477–494, 1981.

G. Burton et al.: "Sodium–retaining activity of some natural and synthetic 21–deoxysteroids" Mol. Pharmacol., vol. 47, pp. 535–543, 1995.

Adriana L. Brachet–Cota et al.: "An Improved preparation of 11,19–oxidopregn–4–ene–3,20–dione and 6,19–oxidopregn–4–ene–3,11,20–trione" Z. Naturforsch., vol. 45b, pp. 711–715, 1990.

Mario D. Galigniana: "Stability study on renal type I mineralocorticoid receptor" Life Science, vol. 59, pp. 511–521, 1996.

Mol. Pharmacol., vol. 52, pp. 749–753 1997.

C. McKittrick: "Regulation of serotonergic function in the CNS by steroid hormones and stress" CNS Neurotransmittersand Neuromodulators, Neuroactive Steroids, pp. 37–76.

W.L. Duax et al.: "The mechanism of action of steroid antagonists: insights from crystallographic studies" J. Steroid Biochem., vol. 31, No. 48, pp. 481–492, 1988.

David H. Wagner, Jr et al.: "Rescue of theymocytes from glucocorticoid–induced cell death mediated by CD28/CTLA–4 costimulatory interactions with B7–1/B7–2" J. Exp. Med., vol. 184, pp. 1631–1638, Nov. 1996.

* cited by examiner

METHOD FOR THE PREPARATION OF 21-HYDROXY-6,19-OXIDOPROGESTERONE (21 OH-6OP)

FIELD OF THE INVENTION

The present invention relates to a novel method of preparing 21-hydroxy-6,19-oxidopro-gesterone (21OH-6OP) and/or its 21-acetate, 21-propionate, 21-hemisuccinate, 21-phosphate and 21-oleate derivatives. 21OH-6OP and its esters are antiglucocorticoids for the treatment or prophylaxis of diseases associated with a glucocorticoid imbalance, in particular for treating Cushing's syndrome or depression.

BACKGROUND OF THE INVENTION

Corticosteroides are steroid hormones related structurally to cholesterol. These hormones are synthesized in the adrenal cortex and include the glucocorticoids (e.g. cortisol), the mineralocorticoids (e.g aldosterone) as well as weak androgens and estrogens. The adrenal function, like that of the thyroid gland, is under the control of the hypothalamus (HPT) and the pituitary (PIT). When cortisol (the naturally-occuring glucocorticoid) levels drop below a setpoint, the hypothalamus releases CRH (corticotropin releasing hormone) which stimulates adrenocorticotropic hormone (ACTH) release from the pituitary. ACTH is a tropic hormone which stimulates the synthesis and secretion of cortisol (it has minimal effects on aldosterone synthesis/secretion), and the growth of the adrenal gland. When cortisol levels increase, this shuts off CRH and ACTH secretion (cf. FIG. 1).

Cortisol is characterized by its properties related to the biosynthesis and metabolism of glucose and propeties related to non-specific as well as specific immunity. Due to their effects on the glucose metabolism, cortisol and natural or synthetic analogues thereof are usually named glucocorticoids. They bind to the glucocorticoid receptor (GR).

The glucocorticoid receptor is a member of a protein super family of closely related intracellular receptors which function as ligand-activated transcription factors. Other members of this super family are the mineralocorticoid receptor (MR) and the progesterone receptor (PR). MR and GR have shown to be highly homologous, thus natural and even synthetic steroids exhibit cross-reaction between these receptors. With respect to PR, its natural ligand progesterone also cross-reacts with MR and GR.

Cushing's syndrome is a disorder resulting from increased adrenocortical secretion of cortisol. Hyperfunction of the adrenal cortex may be ACTH-dependent or it may be independent of ACTH regulation, e.g. production of cortisol by an adrenocortical adenoma or carcinoma. The administration of supraphysiologic quantities of exogenous cortisol or related synthetic analogs suppresses adrenocortical function and mimics ACTH-independent glucocorticoid hyperfunction. ACTH-dependent hyperfunction of the adrenal cortex may be due to hypersecretion of ACTH by the pituitary, secretion of ACTH by a nonpituitary tumor such as small cell carcinoma of the lung (the ectopic ACTH syndrome), or administration of exogenous ACTH. While the term "Cushing's syndrome" has been applied to the clinical picture resulting from cortisol excess regardless of the cause, hyperfunction of the adrenal cortex resulting from pituitary ACTH excess has frequently been referred to as Cushing's disease, implying a particular physiologic abnormality. Patients with Cushing's disease may have a basophilic adenoma of the pituitary or a chromophobe adenoma. Microadenomas can usually be visualized by CT or, preferably, MRI scan, using a high-resolution technique augmented by gadolinium. Some micro-adenomas are difficult to visualize even with these modalities. In some cases, no histological abnormality is found in the pituitary despite clear evidence of ACTH overproduction.

Reference to Cushing's syndrome is herein intended to mean the clinical picture resulting from cortisol excess regardless of the cause, which may be also iatrogenic, both by the injection of ACTH or by the direct administration of cortisol or synthetic analogs such as prednisone, prednisolone, dexamethasone or others that are widely used in various types of diseases including alergic, asthmatic, inflammatory or immunologic. Cushing's syndrome includes in addition adrenal tumours secreting corticoids, ectopic ACTH production and Cushing's disease.

Clinical manifestations include rounded "moon" faces with a plethoric appearance. There is truncal obesity with prominent supraclavicular and dorsal cervical fat pads ("buffalo hump"); the distal extremities and fingers are usually quite slender. Muscle wasting and weakness are present. The skin is thin and atrophic, with poor wound healing and easy bruising. Purple striae may appear on the abdomen. Hypertension, renal calculi, osteo-porosis, glucose intolerance, reduced resistance to infection, and psychiatric disturbances are common. Cessation of linear growth is characteristic in children. Females usually have menstrual irregularities. An increased production of androgens, in addition to cortisol, may lead to hypertichosis, temporal balding, and other signs of virilism in the female.

Although development of antihormonal agents related to the estrogen and androgen receptors has been successful, the search for selective anti-corticoids is more restricted.

Known agents suppressing the synthesis of steroid hormones at various levels (i.e. inhibitors of enzymes which catalyze various stages of the synthesis of steroid hormones) are reviewed in *J.Steroid Biochem.*, vol.5, p.501 (1974) and include the following:

a) derivatives of diphenylmethane, e.g. amphenon B (which suppresses the synthesis of steroid hormones at stages 11-beta-, 17- and 21- of hydroxylase);

b) derivatives of pyridine (SU-c series), e.g. metirapon (which suppresses synthesis at stage 11-beta of hydroxylase);

c) substituted alpha, alpha-glutaramides, e.g. aminoglutetimide (which impedes the synthesis of pregnenolone from cholesterol through suppression of 20-alpha-hydroxylase and $C_{20}$, $C_{22}$-liase;

d) steroid substances e.g. trilostan (3 beta-substituted steroid-3 beta hydroxy-5-androsten-17-one), which suppresses 3 beta-desoxysteroidhydrogenase-5.4-isomerase (*Steroids*, vol.32, p.257).

e) steroids of the spironolactone family which are used as rapidly dissociating anti-Mineralocorticoids (*PNAS USA* 71(4) p. 1431–1435 (1974).

f) a synthetic steroid described as an anti-Mineralocorticoids, ZK91587, showing specific binding properties for the kidney (*Z.Naturforsch.*, 45b, p.711–715 (1990)) and hippocampus type I MR (*Life Science*, 59, p.511–21 (1996)), but not for type II GR. It may therefore be conveniently useful as a tool in the investigation of MR function in tissues containing both receptor systems.

Agents that specifically suppress the interaction of glucocorticoid hormones with hormone receptors are:

a) Mifepriston (11 β, 17β)-11-[4-(Dimethylamino)phenyl]-17-hydroxy-17-(1-propynyl)estra-4,9-dien-3-one, which acts on receptors of glucocorticoid hormones to form a complex incapable of initiating mechanisms leading to glucocorticoid effect (*Annals of New-York Academy of Science*, vol. 761, p.5–28 (1995)).

b) non-steroid substances (*J:Steroid Biochem.*, vol. 31, p.481–492 (1988)) e.g. drotaverina hydrochloride (a derivative of isoquinoline-1-(3.4-dietoxibene zilidene)-6.7-dietoxy-1,2,3,4-tetrahydrizoquinoline) or acetylsalicic acid (*Moskovskaya Meditsina*, 1990, "Receptor mechanisms of the glucocorticoid effect" by V. P. Golikov).

To-date, the only therapeutical application for antiglucocorticoids (e.g. Mifepristone) that has been attempted in a clinical setting is to treat inoperable cases of nonpituitary Cushing's syndrome. In the case of Mifepristone (both an anti-progesterone and an anti-glucocorticoid), high doses (up to 800 mg per day) are required.

Employing a systematic application of strategies to increase activity and decrease cross-reactivity and undesirable side effects, progress has been reported in the development of antihormonal agents with greater potency and selectivity, especially in the antiestrogen and antiandrogen fields.

In EP-903'146 the synthetic steroid, 21-hydroxy-6,19-oxidoprogesterone (21OH-6OP) of formula I,

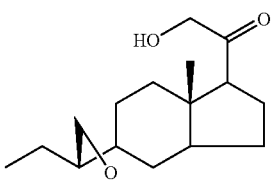

is disclosed as a selective antiglucocorticoid which does not substantially cross-react with uterus-PR or kidney-MR. Said 21-hydroxy-6,19-oxidoprogesterone antiglucocorticoid could be used in the treatment of diseases associated with an excess of glucocorticoids, where an anti-glucocorticoid virtually lacking mineralocorticoid or glucocorticoid properties as well as affinity for MR or PR is desirable.

The synthesis of 21-hydroxy-6,19-oxidoprogesterone (1) and its 21-acetate (2) was first accomplished by Deghenghi in 1966 as intermediate in a synthesis of 19-hydroxy-desoxy-corticosterone, starting from 21-hydroxypregnenolone diacetate. The procedure summarized in Scheme 1 involves the use of a "hypoiodite type" reaction with lead tetraacetate (Pb(AcO)$_4$). Compound 1 was neither isolated nor characterized, but acetylated in situ to acetate 2. Overall yield of partially purified 2 was only 8.3%. Further to the low yield, this method of preparation is generally perceived as being difficult to reproduce notably due to the formation of the chlorohydrin.

Scheme 1:
Synthesis of
21-hydroxy-6,19-oxidoprogesterone
and its 21-acetate derivative by Deghenghi.

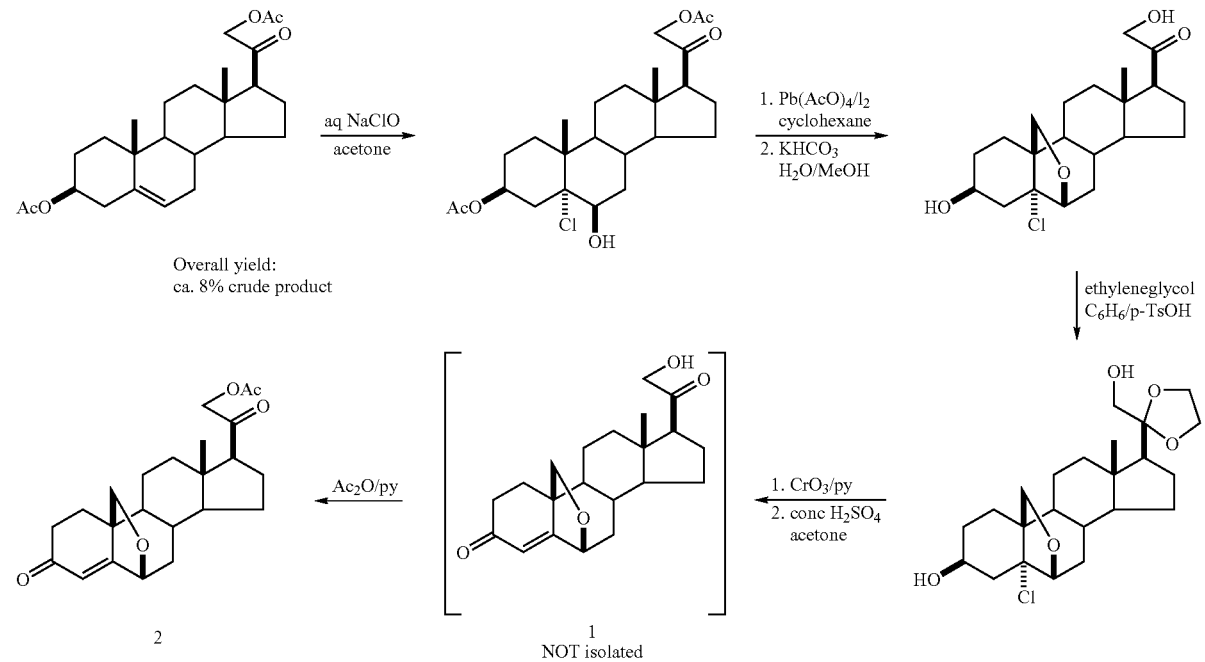

In a more recent synthesis of 19-hydroxydeoxycorticosterone, Kirk and Yeoh (*J. Chem. Soc. Perkin Trans. I*, 2945 (1983)) prepared acetate 2 as an intermediate. This procedure starting from pregnenolone acetate is depicted in Scheme 2. Although full details of the first 3 steps are not given in the experimental section of their publication, according to the literature cited the yield for these steps may be estimated as ca. 34–37% giving an overall yield of acetate 2 of ca. 12% from pregnenolone acetate.

Scheme 2:
Synthesis of
21-hydroxy-6,19-oxidoprogesteroneand its acetate by Kirk et al.

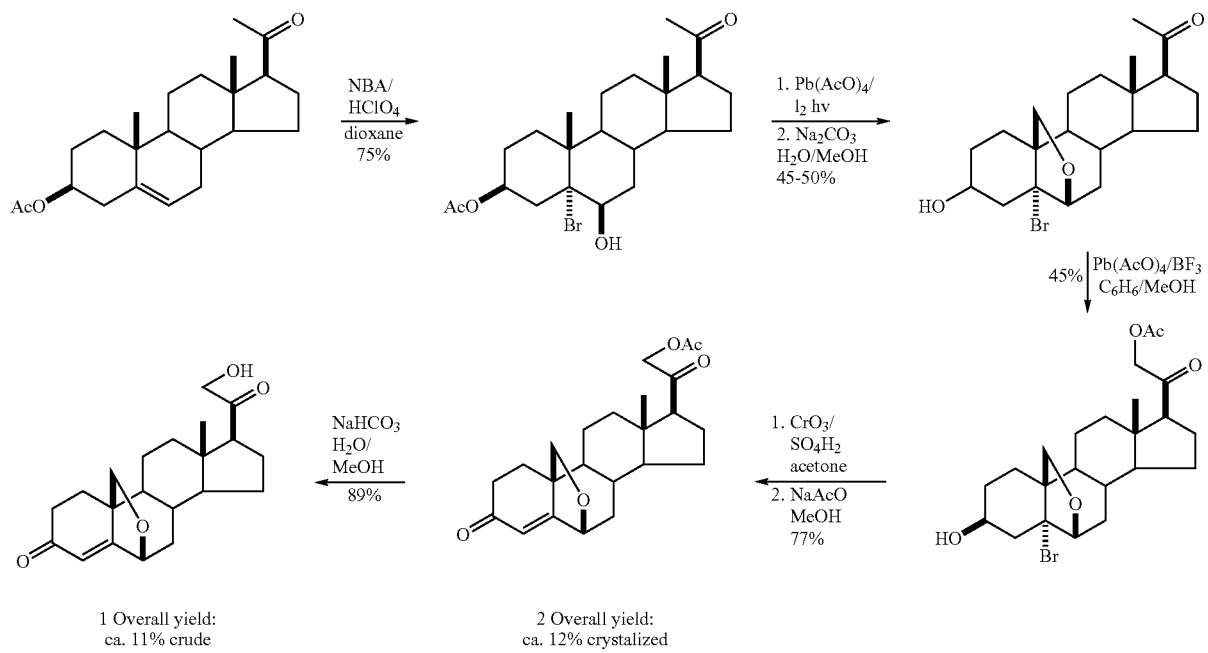

According to a further method, depicted in Scheme 3, the remote functionalization reaction with Pb(AcO)$_4$ and iodine under thermal or photochemical conditions is replaced with the more reproducible and "milder" HgO/iodine system under photochemical conditions and the 21-hydroxylation step is carried out with a hypervalent iodine compound (see A. S. Veleiro, M. V. Nevado, M. C. Monteserin and G. Burton, *Steroids*, 60, 268–272 (1995); M. Akhtar and D. H. R. Barton, *J. Am. Chem. Soc.*, 86, 1528–1534 (1964); R. M. Moriarty, L. S. John and P. C. Du, *J. Chem. Soc. Chem. Commun.*, 641–642 (1981).

Scheme 3:
Synthesis of
21-hydroxy-6,19-oxidoprogesteroneby Veleiro et al.

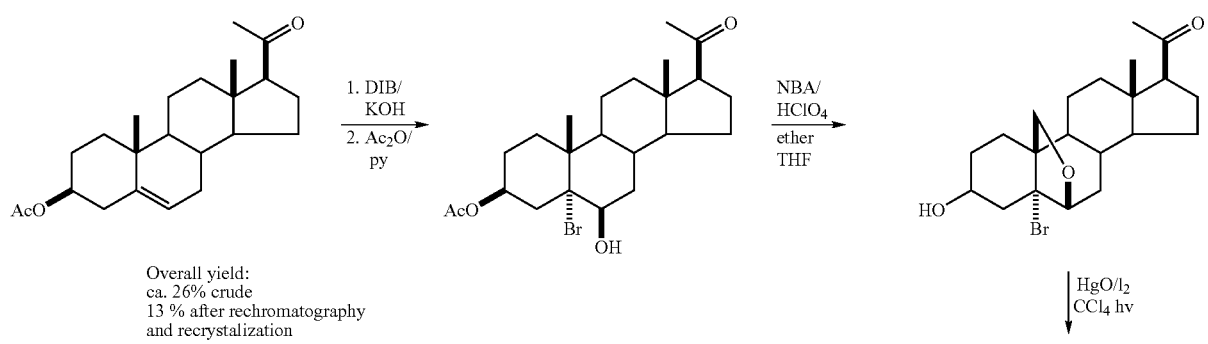

-continued

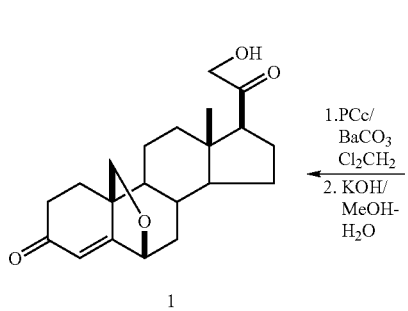
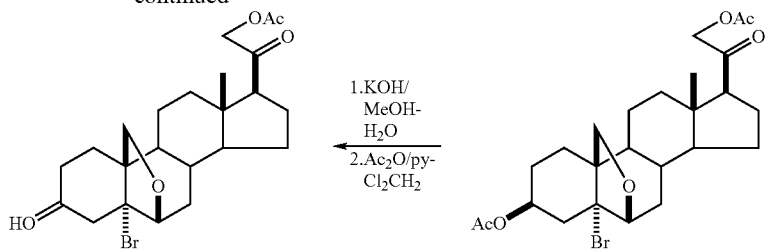

The above procedure starts also from pregnenolone acetate which is first converted into 21-hydroxypregnenolone diacetate. In the best case, overall yield of 1 is ca. 26%; however this product, although apparently pure according to TLC and NMR, could not be crystallized, and thus required additional purification steps by chromatography; yield of pure crystalline 1 is about 13% (19% from 21-hydroxypregnenolone diacetate). Although the acetate 2 is an intermediate in this synthetic route, complete purification could only be achieved after deacetylation (i.e. on compound 1). Furthermore, although this procedure allows the synthesis of small amounts of 1 for the initial biological tests carried out in 1996, attempts to scale up the procedure failed. Although, the currently known methods provide 21-hydroxy-6,19-oxidoprogesterone (1), they consistently give poorer yields as well as byproducts which are difficult to eliminate.

DESCRIPTION OF THE INVENTION

It is an object of the invention to provide a new method for preparing 21-hydroxy-6,19-oxidopro-gesterone (21OH-6OP) and/or its esters.

It is a further object of the invention to provide 21-hydroxy-6,19-oxidoprogesterone and/or its esters.

In a first aspect, the present invention provides a new method of preparing 21-hydroxy-6,19-oxidoprogesterone (1) or its esters, for example carboxylate, phosphate or sulfate esters. In preferred embodiments, the invention provides a new method for preparing 21 OH-6OP and its 21-acetate, 21-propionate, 21-hemisuccinate, 21-phosphate and 21-oleate derivatives. The method of the invention avoids essentially all of the hitherto known inconveniences. The method of the invention produces 21-hydroxy-6,19-oxidoprogesterone (1) in good yield, having an acceptable degree of purity, and avoids heavy metals as reagent. The method of the invention is suitable for large scale industrial preparation of 21-hydroxy-6,19-oxido-progesterone (1) and its esters.

The objects of the invention are met according to the main claim. Preferred embodiments are set out within the dependent claims which are incorporated herewith.

The novel synthetic procedure according to the present invention comprises or consists of the following consecutive basic steps:

a) Providing 21-acetoxypregnenolone (3) (which is actually a commercial product);

b) Transforming the C-3 hydroxy group of 21-acetoxypregnenolone into a labile ester, preferably a formate ester;

c) Obtaining the bromohydrin product from the protected 21-acetoxypregnenolone, said bromohydrin resulting from the addition of a bromine and a hydroxy group onto the double bond of position of C5–C6;

d) Performing an intramolecular cyclisation with the C19 atom with the "Suarez-reagent" (diacetoxyiodobenzene; see Armas et al., *J. Chem.Soc. Perkin I*, 405 (1989)) and iodine under irradiation, thus obtaining the 6,19 oxido-bridge within the scaffold;

e) Performing a selective hydrolysis, preferably with HCl/MeOH/dichloromethane, followed by an oxidation, preferably with pyridinium chlorochromate (PCC), thus obtaining a bromoketone;

f) Performing a hydrolysis of the bromoketone resulting from step e) to obtain 21-hydroxy-6,19-oxidoprogesterone (1), and optionally g) Acylating 21-hydroxy-6,19-oxidoprogesterone (1), to afford the 21-ester (the acetate is shown as 2);

Preferred esters are C1–18 acyl esters (optionally substituted with COOH, 1 or 2 times) and phosphate esters. Acyl esters may be obtained by reacting 21-hydroxy-6,19-oxidoprogesterone (1) with an organic acid, in the presence of a coupling agent (for example N,N'-dicyclohexylcarbodiimide), or with an activated organic ester (for example, a nitrophenol ester), or with an acyl halide (for example, an acyl chloride), or with an acyl anhydride. Phosphate esters may be obtained by reacting 21-hydroxy-6,19-oxidoprogesterone with a phosphorylating agent (for example phosphorus oxychloride, followed by basic hydrolysis).

The 21-propionate or 21-hemisuccinate, and 21-oleate and derivatives are obtained by esterifying 21-hydroxy-6,19-oxidoprogesterone (1) of step f) with propionic acid, succinic or oleic acid, their anhydrides, activated esters or acyl chlorides.

A preferred synthetic procedure according to the present invention is depicted in Scheme 4.

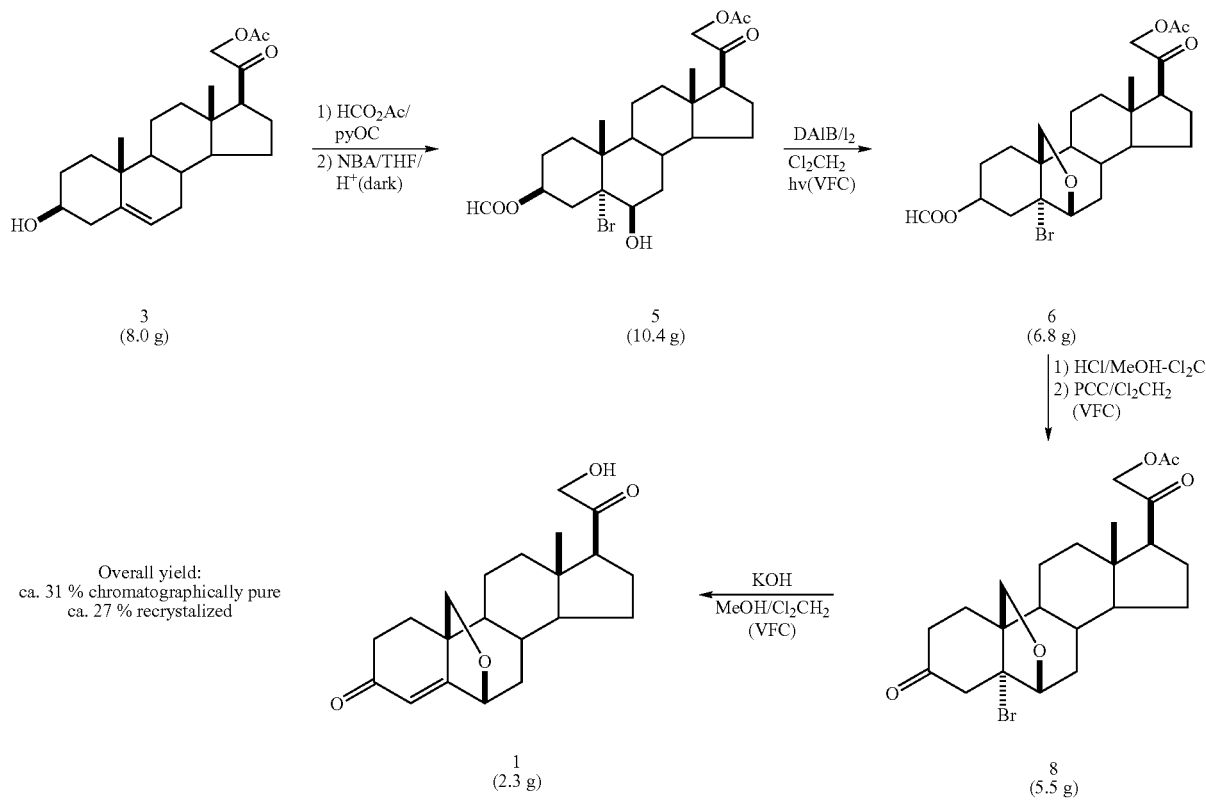

Scheme 4:
Novel Synthesis of 21-hydroxy-6,19-oxidoprogesterone

According to the preferred method illustrated in Scheme 4, a formate group is introduced as protecting group for position 3. Formates have the advantage that they may be hydrolized under relatively mild acid conditions (HCl/MeOH-dichloromethane) in which primary acetates and even α-acetoxy-ketones are stable. The introduction of a formate moiety is preferably carried out under very mild conditions using preferably mixed acetic-formic anhydride (prepared in situ from formic acid and acetic anhydride). The bromo-hydrin formation, is carried out with N-bromoacetamide in THF yielding 80% of the desired bromohydrin 5 and about 20% of the 5α-HO-6β-Br isomer. The mixture may be separated by crystallization or Thin Layer Chromatography. For the intramolecular cyclisation involving C-$_{19}$, the "Suarez reagent" (diacetoxyiodobenzene (DAIB)) and iodine is employed as the "hypoiodite" as generating system under suitable irradiation—preferably with a standard tungsten lamp.

Quite surprisingly, it turns out that upon performing the intramolecular cyclisation step in di-chloromethane (CH$_2$Cl$_2$), the reaction is not only rapid (complete conversion in less than 1 hour) and clean, but also excellent yields could be obtained.

Temperature control (25° C.) of the cyclisation step, achieved by using a glass jacketed reactor with water circulation, increases the yield and diminishes excessive oxidation by-products. Furthermore, epoxide formation is eliminated, the isomeric bromohydrin is inert to the reagent and could be easily separated (together with the iodobenzene side product) from the desired bromoether 6 by vacuum filtration through a silica gel column (VFC).

The selective hydrolysis of the formate ester, is preferably performed with HCl in MeOH-dichloromethane, followed by an oxidation, preferably with PCC, thus affording the bromoketone 8. This product partially eliminates HBr to give the unsaturated ketone (2) when subjected to VFC (very short silica gel column) purification, however this poses no problem as the unsaturated product is the desired product of the following step, in which the treatment with a base deacetylates position 21 and completes the elimination of the C-5 bromine thus giving the desired pro-duct (1).

Purification of 1 may be achieved with a fast VFC through a short silica gel column to afford chromatographically pure product in over 31% yield. This may be crystallized from absolute ethanol to yield crystalline 1 in 27% yield.

The 21-acetate (2) is prepared by standard acetylation of 1 with acetic anhydride in pyri-dine. The acetate is recrystallized from absolute ethanol.

The novel synthesis according to the present invention has the following advantages:
 a) It eliminates the need of the selective acetylation step or any need to differentiate the hydroxyl groups at C-21 and C-3.
 b) It modifies the hypoiodite reaction so that no heavy metals are required (lead, silver or mercury based reagents) and it proceeds under homogeneous conditions, thus allowing a scale up to multigram and eventually kilogram amounts.
 c) It reduces the secondary products formed at different stages (specially 5,6-epoxide formation) so as to minimize the purification steps, and specially to avoid or minimize the need of column chromatography on silica gel, as bromoethers, compound 1 and 2 are intrinsically unstable under these conditions.

d) It reduces reaction volumes throughout to allow scale up.

Starting from compound 1, synthesis of acyl esters, such as 21-propionate (2a), and 21-hemisuccinate (2b) and 21-oleate (2c)-6,19-oxidoprogesterone derivatives can be performed as illustrated in Scheme 5.

Also shown in Scheme 5 is the preparation of the 21-phosphate derivative (2d).

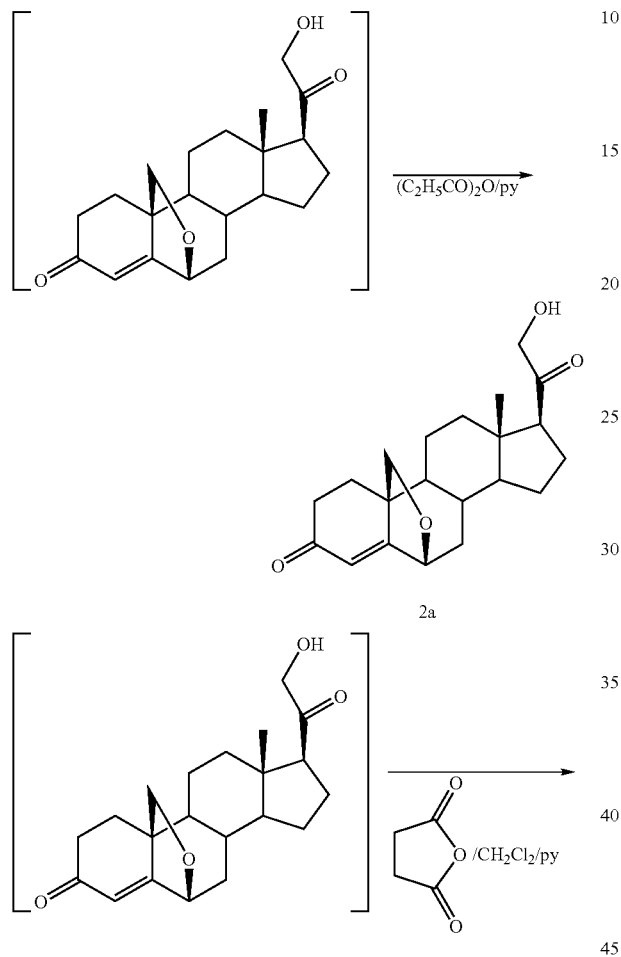

2a

The compounds synthesised according to the present invention are for use as a medicament, alone or in combination with pharmaceutically acceptable carriers and/or excipients. Such medicament is notably suitable in the manufacture of a medicament for the treatment or prophylaxis of diseases associated with an excess of glucocorticoids, e.g. for the treatment of Cushing's syndrome, iatrogenic hypercortisolism or depression.

The invention will now be described, by way of illustration only, with reference to the following examples:

EXAMPLES

Materials and Methods

Melting points were taken on a Fisher-Johns apparatus and are uncorrected. IR spectra were recorded in thin films using KBr disks on a Nicolet Magna IR 550 FT-IR spectrometer. $^1H$ and $^{13}C$ NMR spectra were measured in Bruker AC-200 or AM-500 NMR spectrometers in deuteriochloroform (using TMS as internal standard). The J values are given in Hz. Spectra were assigned by analysis of the DEPT, COSY 45 and HETCOSY spectra and by comparison with those of progesterone.

The electron impact mass spectra (EI) were measured in a VG Trio 2 mass spectrometer at 70 eV by direct inlet. FAB mass spectra and electron impact high resolution mass spectra (HRMS) were obtained in a VG ZAB BEQQ mass spectrometer. All solvents used were reagent grade. Solvents were evaporated at ca. 45° C. under vacuum. Zinc dust was activated by suspending in 1M HCl, washing with water, absolute ethanol and diethyl ether and drying 2 h at 120° C. The homogeneity of all compounds was confirmed by thin layer chromatography.

Large Scale Synthesis of 21-hydroxy-6,19-oxidoprogesterone (1)

Structures of starting material, intermediates and final products (1) and (2):

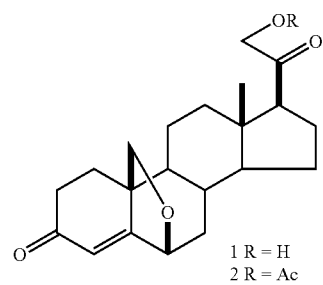

1 R = H
2 R = Ac

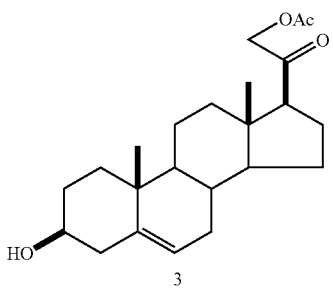

3

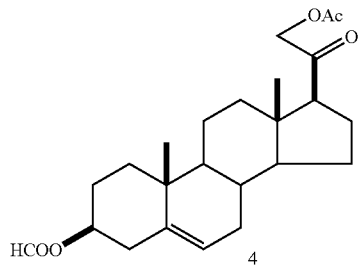

4

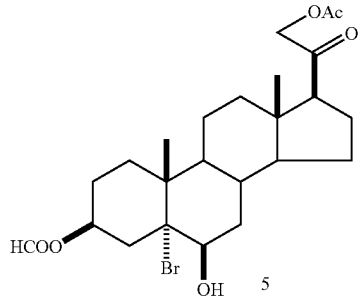

5

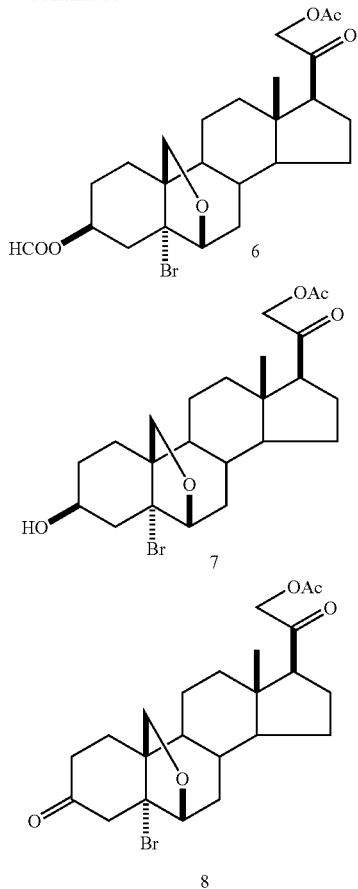

3β-Formyloxy-21-acetyloxy-5-pregnen-20-one (4)

Acetic anhydride (13.4 ml) is added dropwise to formic acid (6.6 ml) at 0° C., the solution is heated at 50° C. for 15 min and cooled rapidly to 0° C. The resulting acetoformic anhydride solution is added dropwise to a stirred suspension of 21-acetoxypregnenolone (3, 8.0 g) in dry pyridine (20.8 ml) at 0° C., and stirring is continued at that temperature for 2 h. The reaction product is poured over cold saturated aqueous sodium bicarbonate solution, filtered and the solid is washed with saturated aqueous sodium bicarbonate solution, water and 1N HCl and water (until neutral) rendering formate 4 (8.0 g); $^1$H NMR (200.13 MHz) $\delta_H$ 0.70 (3H, s, 13-CH$_3$), 1.02 (3H, s, 10-CH$_3$), 2.16 (3H, s, 21-CH$_3$CO), 2.53 (1H, t, J=8.0 Hz, 17-H), 4.50 (1H, d, J=17.0 Hz, 21a-H), 4.70 (1H, d, J=17.0 Hz, 21b-H), 5.32 (1H, m, 3-H), 5.38 (1H, d, J=3.0 Hz, 6-H), 8.02 (1H, s, HCOO).

3β-Formyloxy-5α-bromo-6β-hydroxy-21-acetyloxypregnan-20-one (5)

Formate 4 (8.0 g), is dissolved in diethyl ether (100 ml) and THF (37.2 ml) and cooled to 10° C. To the stirred solution at 10–15° C.—which protected from light—7.5% perchloric acid (11.88 ml) is added, followed by N-bromoacetamide (4.75 g) in 8 portions over a 25 min period. Stirring is continued for 45 min at 25° C. and the reaction is stopped by addition of 10% aqueous sodium thiosulfate solution until complete decoloration. The reaction mixture is then extracted with dichloromethane/methanol 10:1 and the organic layer, is washed with water, dried with anhydrous sodium sulfate and the solvent is evaporated to afford bromohydrin 5 (10.4 g, containing about 20% of the 5α-hydroxy-6β-bromo isomer as determined by $^1$H NMR).

3β-Formyloxy-5α-bromo-21-acetyloxy-6,19-oxidopregnan-20-one (6)

Nitrogen is bubbled for 5 min through a solution of bromohydrin compound 5 (10.4 g, containing about 20% of the 5α-hydroxy-6β-bromo isomer) in freshly distilled dichloro-methane (723 ml) contained in a 1 liter glass vessel fitted with an external cooling jacket with circulating water at 25° C. and magnetic stirrer. Diacetoxyiodobenzene (Suarez reagent, 7.66 g) and iodine (5.46 g) are successively added with stirring. The vessel is exposed to two 300 Watt tungsten lamps (5000 lm each) and vigorous stirring is continued for 1 h at 25° C. Irradiation is turned off and a saturated aqueous solution of sodium thiosulfate is added until complete decoloration. The organic layer is separated, dried with anhydrous sodium sulfate and the solvent evaporated. The resulting solid is dissolved in dichloro-methane (8 ml) and applied to a silicagel G-60 column (12 cm diameter×8 cm height) previously flushed with hexane; successive elution (applying vacuum to the outlet) with hexane-ethyl acetate 9:1 (1100 ml), 8:2 (700 ml), 7:3 (700 ml) and 6:4 (600 ml) affords 31×100 ml fractions. Fractions are analyzed by TLC and those containing bromoether 6 are pooled and evaporated to dryness to afford 6 (6.8 g). $^1$H NMR (200.13 MHz) $\delta_H$ 0.70 (3H, s, 13-CH$_3$), 2.16 (3H, s, 21-CH$_3$CO), 2.52 (1H, t, J=8.8 Hz, 17-H), 3.73 (1H, d, J=8.4 Hz, 19a-H), 3.94 (1H, d, J=8.4 Hz, 19b-H), 4.08 (1H, d, J=4.2 Hz, 6-H), 4.50 (1H, d, J=16.8 Hz, 21a-H), 4.71 (1H, d, J=16.8 Hz, 21b-H), 5.34 (1H, m, 3-H), 8.02 (1H, s, HCOO).

3β-Hydroxy-5α-bromo-21-acetyloxy-6,19-oxidopregnan-20-one (7)

A stirred solution of the bromoether 6 (6.8 g) obtained above, is dissolved in dichloro-methane (45.7 ml) and methanol (154.7 ml) and is cooled to 0° C. in an ice bath and water (10.9 ml) while conc. HCl (23.0 ml) is added. After about 30 min of vigorous stirring at 0° C. (disappearance of the starting material is monitored by TLC) the reaction mixture is neutralized with 20% aqueous sodium hydroxide and extracted with dichloromethane. The organic layer is dried with anhydrous sodium sulfate and the solvent evaporated to afford the alcohol compound 7 (6.5 g); $^1$H NMR (200.13 MHz) $\delta_H$ 0.69 (3H, s, 13-CH$_3$), 2.16 (3H, s, 21-CH$_3$CO), 2.52 (1H, t, J=8.5 Hz, 17-H), 3.62 (1H, d, J=8.5 Hz, 19a-H), 3.92 (1H, d, J=8.5 Hz, 19b-H), 4.07 (1H, d, J=4.0 Hz, 6-H), 4.15 (1H, m, 3-H), 4.51 (1H, d, J=17.0 Hz, 21a-H), 4.70 (1H, d, J=17.0 Hz, 21b-H).

5α-Bromo-21-acetyloxy-6,19-oxidopregnane-3,20-dione (8)

A suspension of pyridinium chlorochromate (12.1 g), barium carbonate (5.0 g) and 3 Å molecular sieves (9.60 g), in dry dichloromethane (480 ml) is stirred under nitrogen for 10 min. To the resultant orange slurry a solution of bromoether 7 (6.5 g) obtained above in dry dichloromethane (324 ml) is added and stirring is continued for about 90 min, until the starting material (TLC) has disappeared. The reaction mixture is percolated through a short silicagel G 60 column (12 cm diameter×8 cm height) washed with diethyl ether (2×150 ml) and hexane-ethyl acetate 1:2 (3×150 ml). Fractions containing the product are pooled and evaporated to dryness affording 5.5 g of ketone 8 (containing about 10% of Δ$^4$-3-ketone (2); $^1$H NMR (200.13 MHz) $\delta_H$ 0.70 (3H, s, 13-CH$_3$), 2.16 (3H, s, 21-CH$_3$CO), 2.51 (1H, t, J=8.5 Hz, 17-H), 2.85 (1H, d, J=16.0 Hz, 4a-H), 3.40 (1H, d, J=16.0 Hz, 4b-H), 3.90 (1H, d, J=9.0 Hz, 19a-H), 4.07 (1H, d, J=4.0 Hz, 6H), 4.15 (1H, d, J=9.0 Hz, 19b-H), 4.50 (1H, d, J=17.0 Hz, 21a-H), 4.71 (1H, d, J=17.0 Hz, 21b-H).

21-Hydroxy-6,19-oxido-4-pregnene-3,20-dione (1)

The ketone 8 (5.5 g) obtained from the preceding step is dissolved in methanol (263.8 ml) and dichloromethane (13.2 ml). To the stirred solution 14% methanolic KOH (53.4 ml) is added and stirring is continued at room temperature for about 15 min, until the starting material (TLC) has disappeared. The reaction mixture is neutralized with 1N HCl and extracted with dichloromethane. The organic layer is dried with anhydrous sodium sulfate and the solvent is evaporated thus yielding crude 21-hydroxy-6,19-oxidoprogesterone (1, 4,6 g). The solid is dissolved in dichloromethane (5 ml) and sent through to a silicagel G-60 column (8.5 cm diameter×5 cm height) previously flushed with hexane-ethyl acetate 7:3; successive elution (applying vacuum to the outlet) with hexane-ethyl acetate 6:4 (1350 ml) and 1:1 (900 ml) affords 30 fractions. The fractions are analyzed by TLC and those containing 1 are pooled and evaporated to dryness to afford 21-hydroxy-6,19-oxidoprogesterone (1, 2.3 g). $^1$H NMR (200.13 MHz) $\delta_H$ 0.74 (3H, s, 13-CH$_3$), 2.45 (1H, t, J=8.5 Hz, 17-H), 3.51 (1H, d, J-=8.8 Hz, 19a-H), 4.18 (3H, s, 21-CH$_3$), 4.20 (1H, d, J=8.8 Hz, 19b-H), 4.69 (1H, d, J=5.0 Hz, 6-H), 5.82 (1H, s, 4-H).

Re-crystallization from absolute ethanol affords a first crop of crystalline 1 (1.27 g), mp 165–166° C. The mother liquor is concentrated to yield a second crop of 1 (0.68 g).

21-Acetyloxy-6,19-oxido-4-pregnene-3,20-dione (2)

Crude 21-hydroxy-6,19-oxidoprogesterone (1, 2 g before chromatographic purification) was dissolved in dry pyridine (15.6 ml) and acetic anhydride (15.6 ml) added. The solution was stirred for 90 min at 25° C., poured over 1M HCl and filtered (alternatively the solid may be extracted with dichloromethane). The solid was washed with water (until neutral), dried, dissolved in dichlorometane (2 ml) and applied to a silicagel G-60 column (7 cm diameter×5 cm height) previously flushed with hexane-ethyl acetate 7:3; succesive elution (applying vacuum to the outlet) with hexane-ethyl acetate 7:3 (700 ml) and 6:4 (700 ml) afforded 20 fractions. Fractions were analyzed by TLC and those containing 2 pooled and evaporated to dryness to afford 21-acetyloxy-6,19-oxidoprogesterone (2, 1.12 g). Recrystallization from absolute ethanol (with drops of methanol) afforded crystaline 2 (0.72 g), mp 190–191° C. $^1$H NMR (200.13 MHz) $\delta_H$ 0.76 (3H, s, 13-CH$_3$), 2.17 (3H, s, 21-CH$_3$CO), 2.51 (1H, t, J=8.5 Hz, 17-H), 3.51 (1H, d, J=8.2 Hz, 19a-H), 4.20 (1H, d, J=8.2 Hz, 19b-H), 4.50 (1H, d, J=16.7 Hz, 21a-H), 4.69 (1H, d, J=5.0 Hz, 6-H), 4.72 (1H, d, J=16.7 Hz, 21b-H), 5.82 (1H, s, 4-H).

21-Propanoyloxy-6,19-oxido-4-pregnene-3,20-dione (2a)

Crude 21-hydroxy-6,19-oxidoprogesterone (1, 0.2 g before chromatographic purification) was dissolved in dry pyridine (0.28 ml) and propanoic anhydride (0.2 ml) added. The solution was stirred for 1 h at 25° C., methanol was added to destroy excess anhydride and the solution concentrated in vacuo. The residue was diluted with dichloromethane, washed with 1M HCl and water, and evaporated to dryness (0.233 g). Purification as above afforded 21-propanoyloxy-6,19-oxidoprogesterone (2a, 0.116 g). $^1$H NMR (200.13 MHz) $\delta_H$ 0.76 (3H, s, 13-CH$_3$), 1.18 (3H, t, J=7.6 Hz, 21-CH$_3$CH$_2$CO), 2.46 (2H, q, J=7.6 Hz, 21-CH$_3$CH$_2$CO), 2.51 (1H, t, J=8.0 Hz, 17-H), 3.51 (1H, d, J=8.2 Hz, 19a-H), 4.20 (1H, d, J=8.2 Hz, 19b-H), 4.50 (1H, d, J=16.8 Hz, 21a-H), 4.70 (1H, d, J=5.0 Hz, 6-H), 4.73 (1H, d, J=16.8 Hz, 21b-H), 5.82 (1H, s, 4-H). EIMS m/z 400 (17) [M]$^+$, 342 (5), 313 (24), 285 (23), 267 (10), 57 (100).

21-Succinoyloxy-6,19-oxido-4-pregnene-3,20-dione (2b)

21-hydroxy-6,19-oxidoprogesterone (1, 0.75 g) was dissolved in dry dichloromethane (37.5 ml) and pyridine (1.9 ml) and succinic anhydride (0.75 g) added. The solution was stirred for 4 h at 25° C., a second portion of succinic anhydride (0.375 g) added and stirring continued for 6 h (until disappearance of starting material). The reaction mixture was concentrated, and the residue extracted with diethyl ether. The ethereal solution was washed with 1M HCl and extracted with aqueous 10% sodium carbonate. The aqueous layer was acidified with conc. HCl to pH=3 and extracted with dichloromethane. Washing with water and evaporation to dryness afforded crude 21-succinoyloxy-6,19-oxidoprogesterone (2b, 0.823 g). The solid was dissolved in dichloromethane (1 ml) and applied to a silicagel G-60 column (6 cm diameter×4 cm height) previously flushed with hexane-ethyl acetate 2:8; succesive elution (applying vacuum to the outlet) with hexane-ethyl acetate 2:8 (200 ml) and ethyl acetate (500 ml) afforded 14 fractions. Fractions were analyzed by TLC and those containing 2b pooled and evaporated to dryness to afford 21-succinoyloxy-6,19-oxidoprogesterone (2b, 0.455 g). $^1$H NMR (200.13 MHz) $\delta_H$ 0.75 (3H, s, 13-CH$_3$), 2.52 (1H, t, J=8.0 Hz, 17-H), 2.75 (4H, m, 21-HCOOCH$_2$CH$_2$CO), 3.51 (1H, d, J=8.2 Hz, 19a-H), 4.20 (1H, d, J=8.2 Hz, 19b-H), 4.54 (1H, d, J=16.9 Hz, 21a-H), 4.70 (1H, d, J=5.0 Hz, 6-H), 4.75 (1H, d, J=16.9 Hz, 21b-H), 5.82 (1H, s, 4-H). EIMS m/z 444 (3) [M]$^+$, 344 (24), 313 (55), 285 (44), 267 (17), 91 (60), 79 (54), 55 (100).

21-Oleoyloxy-6,19-oxido-4-pregnene-3,20-dione (2c)

21-hydroxy-6,19-oxidoprogesterone (1, 0.052 g) was dissolved in dry dichloromethane (1 ml) and pyridine (0.12 ml) and oleoyl chloride (0.1 ml) added. The solution was stirred for 24 h at 25° C., diluted with dichloromethane, washed with 1M HCl and water, and evaporated to dryness. Purification by preparative TLC afforded 21-oleoyloxy-6,19-oxidoprogesterone (2c, 0.075 g). $^1$H NMR (200.13 MHz) $\delta_H$ 0.76 (3H, s, 13-CH$_3$), 0.88 (3H, t, J=7.0 Hz, CH$_3$—CH—CO), 2.34 (2H, t, J=7.7 Hz, CH—CH$_2$CO), 2.50 (1H, t, J=8.5 Hz, 17-H), 3.51 (1H, d, J=8.3 Hz, 19a-H), 4.20 (1H, d, J=8.3 Hz, 19b-H), 4.49 (1H, d, J=16.9 Hz, 21a-H), 4.70 (1H, d, J=4.5 Hz, 6-H), 4.73 (1H, d, J=16.9 Hz, 21b-H), 5.34 (2H, m, CH—CH=CH—CH—CO), 5.82 (1H, s, 4-H).

21-Phosphate-6,19-oxido-4-pregnene-3,20-dione (2d)

21-hydroxy-6,19-oxido-4-pregnene-3,20-dione (1, 0.052 g) was dissolved in dry dichloromethane (1 ml) and pyridine (0.12 ml), and phosphochloridic acid diallyl ester (0.024 g, 1 eq.) was added dropwise at 0° C., over 30 minutes. The mixture was allowed to warm to room temperture and stirred overnight. The mixture was washed three times with 5% NaHCO$_3$, the organic layer was dried and evaporated in vacuo without heating. To the resulting syrup was added a solution of NaOH (2,2 equivalents) in water (3 ml). The solution was brought slowly to reflux, and gently refluxed for 12 hours. Lyophilization yielded the crude phosphate disodium salt, which was recrystallized from ethanol. Alternatively, the crude disodium salt may be dissolved in water, and the pH adjusted with HCl, to cause precipitation of the free phosphate.

What is claimed is:

1. A method of preparing 21-hydroxy-6,19-oxidoprogesterone (1) or an acyl or phosphate derivative thereof.

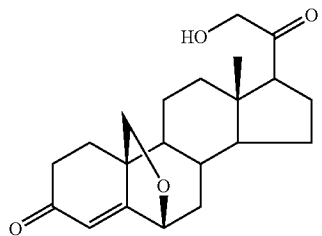

(1)

the method comprising
a) protecting the C-3 hydroxy group of 21-acetoxypregnenolone through formation of a labile ester;
b) obtaining the bromohydrin product thereof, by addition of a bromine and a hydroxy group onto the double bond of position of C5–C6 of the ester protected 21-acetoxy-pregnenolone;
c) performing an intramolecular cyclization with the C19 atom with the "Suarez-reagent" (diacetoxyiodobenzene) and iodine under irradiation, thus obtaining the 6,19 oxido-bridge within the scaffold;
d) performing a selective hydrolysis, followed by an oxidation, to obtain a bromo-ketone;
e) performing a hydrolysis of the bromoketone resulting from step d) to obtain 21-hydroxy-6,19-oxidoprogesterone (1); and optionally
f) reacting compound (1) with an acylating agent or phosphorylating agent.

2. The method according to claim 1, wherein the 21-acetate derivative is obtained by acetylating 21-hydroxy-6,19-oxidoprogesterone (1) of e).

3. The method according to claim 1, wherein a C1–18 acyl derivative is obtained by esterifying 21-hydroxy-6,19-oxidoprogesterone with a C1–18 acid, anhydride, active ester or acyl chloride.

4. The method according to claim 1, wherein a 21-propionate, 21-hemisuccinate, a 21-phosphate, or a 21-oleate derivative is obtained by esterifying 21-hydroxy a -6,19-oxidoprogesterone (1) of e) with propionic acid, succinic acid, oleic acid or their anhydrides or active esters or acid chlorides.

5. The method according to claim 1, wherein the 21-phosphate derivative is obtained by reacting oxidoprogesterone (1) of e) with a phosphorylating agent.

6. The method according to claim 1 wherein for a) a formate ester is afforded.

7. The method according to claim 1, wherein the intramolecular cyclisation c) is performed in dichloromethane as solvent.

8. The method according to claim 1, wherein the selective hydrolysis of d) is performed with HCl in MeOH/dichloromethane as solvent.

9. The method according to claim 1, wherein the oxidation in d) is performed with pyridinium chlorochromate (PCC).

10. The method according to claim 1, wherein the hydrolysis in e) is performed with KOH in MeOH/dichloromethane as solvent. intramolecular cyclisation is carried out in CH2Cl2.

11. A method for preparing (6)

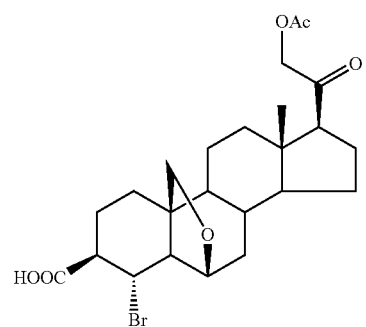

(6)

comprising the step of performing an intramolecular cyclisation between the 6-OH and the $C_{19}$ of the molecule (5)

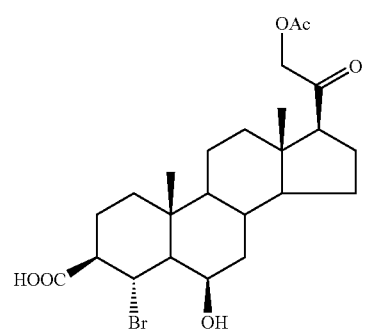

(5)

comprising the step of performing an intramolecular cyclisation between the 6-OH and the C19 of the molecule (5) by photoreaction with diacetoxyiodobenzene and $I_2$.

12. A method accoding to claim 11, wherein the intramolecular cyclisation is carried ou in $CH_2Cl_2$.

* * * * *

UNITED STATES PATENT AND TRADEMARK OFFICE
CERTIFICATE OF CORRECTION

PATENT NO. : 7,071,328 B2
APPLICATION NO. : 10/380167
DATED : July 4, 2006
INVENTOR(S) : Gerardo Burton et al.

It is certified that error appears in the above-identified patent and that said Letters Patent is hereby corrected as shown below:

Col. 16 and 17 Claim 1 should read:
Claim 1. A method of preparing 21-hydroxy-6,19-oxidoprogesterone (1) or an acyl or phosphate derivative thereof [[.]]

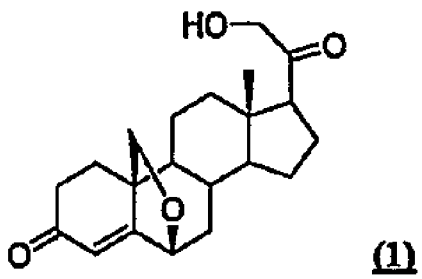

(1)

the method comprising
a) protecting the C-3 hydroxy group of 21-acetoxypregnenolone through formation of a labile ester;
b) obtaining the bromohydrin product thereof, by addition of a bromine and hydroxy group onto the double bond of position of C5-C6 of the ester protected 21-acetoxy-pregnenolone;
c) performing an intramolecular cyclization with the C19 atom with the "Suarez-reagent" (diacetoyiodobenzene) and iodine under irradiation, thus obtaining the 6,19 oxido-bridge within the scaffold;
d) performing a selective hydrolysis, followed by an oxidation, to obtain a bromo-ketone; e) performing a hydrolysis of the bromoketone resulting from step d) to obtain 21-hydroxy-6,19-oxidoprogesterone (1); and optionally
f) reacting compound (1) with an acylating agent or phosphorylating agent.

Col. 17 Claim 4 should read:
Claim 4. The method according to claim 1, wherein a 21-propionate, a 21-hemisuccinate, a 21-phosphate, or a 21-oleate derivative is obtained by esterifying 21-hydroxy [[a]] -6,19-oxidoprogesterone (1) of e) with propionic acid, succinic acid, oleic acid or their anhydrides or active esters or acid chlorides.

Col. 18 Claim 10 should read:
Claim 10. The method according to claim 1, wherein the hydrolysis is e) is performed with KOH in MeOH/dichloromethane as solvent. ~~intramolecular cyclisation is carried out in CH2Cl2.~~

Col. 18 Claim 11 should read:
Claim 11. A method for preparing (6)

UNITED STATES PATENT AND TRADEMARK OFFICE
CERTIFICATE OF CORRECTION

PATENT NO.      : 7,071,328 B2                                    Page 2 of 3
APPLICATION NO. : 10/380167
DATED           : July 4, 2006
INVENTOR(S)     : Gerardo Burton et al.

It is certified that error appears in the above-identified patent and that said Letters Patent is hereby corrected as shown below:

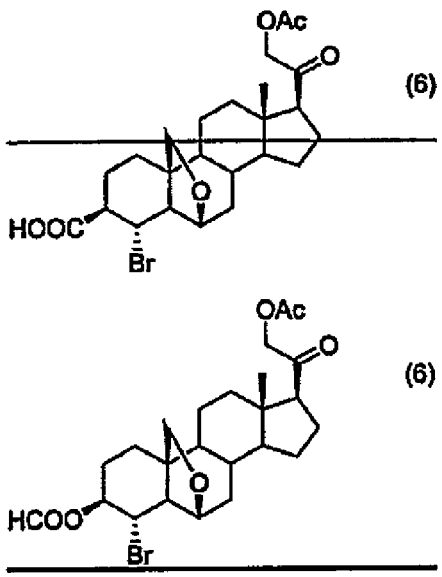

comprising the step of performing an intramolecular cyclisation between the 6-OH and the $C_{19}$ of the molecule (5)

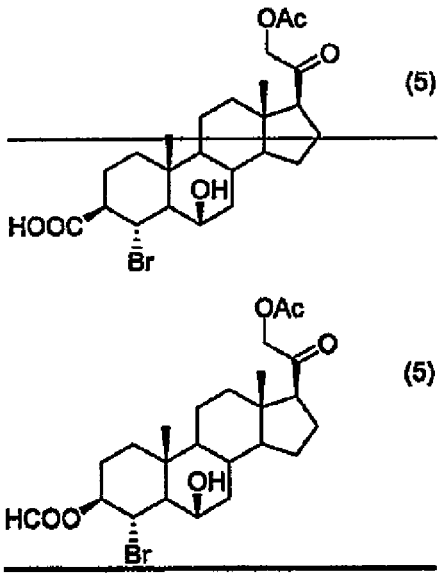

~~comprising the step of performing an intramolecular cyclisation between the 6-OH and the of the molecule (5)~~ by photoreaction with diacetoxyiodobenzene and $I_2$.

UNITED STATES PATENT AND TRADEMARK OFFICE
CERTIFICATE OF CORRECTION

PATENT NO. : 7,071,328 B2
APPLICATION NO. : 10/380167
DATED : July 4, 2006
INVENTOR(S) : Gerardo Burton et al.

It is certified that error appears in the above-identified patent and that said Letters Patent is hereby corrected as shown below:

Col. 18 Claim 12 should read:
Claim 12. [[A]] <u>The</u> method accoding to claim 11, wherein the intramolecular cyclisation is carried ~~ou~~ <u>out</u> in $CH_2Cl_2$.

Signed and Sealed this

Sixteenth Day of January, 2007

JON W. DUDAS
*Director of the United States Patent and Trademark Office*